United States Patent [19]
Shay et al.

[11] Patent Number: 5,639,613
[45] Date of Patent: Jun. 17, 1997

[54] METHODS FOR CANCER DIAGNOSIS AND PROGNOSIS

[75] Inventors: Jerry Shay, Dallas, Tex.; Michael David West, Belmont, Calif.; Woodring E. Wright, Arlington, Tex.

[73] Assignee: Board of Regents, University of Texas System, Austin, Tex.

[21] Appl. No.: 423,403

[22] Filed: Apr. 18, 1995

Related U.S. Application Data

[63] Continuation-in-part of Ser. No. 315,216, Sep. 28, 1994, which is a continuation-in-part of Ser. No. 255,774, Jun. 7, 1994, which is a continuation-in-part of Ser. No. 151,477, Nov. 12, 1993, and a continuation-in-part of Ser. No. 153,051, Nov. 12, 1993, which is a continuation-in-part of Ser. No. 60,952, May 13, 1993, which is a continuation-in-part of Ser. No. 38,766, Mar. 24, 1993, Pat. No. 5,489,508, which is a continuation-in-part of Ser. No. 882,438, May 13, 1992, abandoned, said Ser. No. 151,477, is a continuation-in-part of Ser. No. 60,952, May 13, 1993.

[51] Int. Cl.$^6$ .............................. C12Q 1/68; C12P 19/34
[52] U.S. Cl. ........................ 435/6; 435/91.2; 435/183; 435/184; 435/194; 436/63; 436/64; 935/77; 935/78
[58] Field of Search ................... 435/6, 194, 91.2, 435/183, 184; 436/63, 64; 935/77, 78

[56] References Cited

FOREIGN PATENT DOCUMENTS

WO 93/23572 11/1993 WIPO.

OTHER PUBLICATIONS

Hiyama et al, J National Cancer Institute (Jan. 1996) 88:116–122.
Chadeneau et al, Oncogene (1995) 11:893–898.
Haaly, Oncology Research (1995) 7:121–130.
Bacchetti et al, International Journal Oncology (1995) 7:423–432.
Tahara et al, Clinical Cancer Research (1995) 1:1245–1251.
Blackburn et al. (1989), "Recognition and Elongation of Telomeres by Telomerase" *Genome*, 31:553–560.
Blackburn, (May 1991), "Structure and Function of Telomeres", *Nature*, 350:569–573.
Counter et al. (May 1992), "Telomere Shortening Associated with Chromosome Instability is Arrested in Immortal Cells Which Express Telomerase Activity" *The EMBO Journal*, 11(5):1921–1929.
Counter et al. (May 1994), "Stabilization of Short Telomeres and Telomerase Activity Accompany Immortalization of Epstein–Barr Virus–Transformed Human B Lymphocytes" *Journal of Virology*, 68(5):3410–3414.
Counter et al., (Apr. 1994), "Telomerase Activity in Human Ovarian Carcinoma" *Proc. Natl. Acad. Sci. USA*, 91:2900–2904.
Greider and Blackburn, (1987), "The Telomere Terminal Transferase of Tetrahymena Is a Ribonucleoprotein Enzyme with Two Kinds of Primer Specificity", *Cell*, 51:887–898.
Greider and Blackburn, (1989), "A Telomeric Sequence in the RNA of Tetrahymena Telomerase Required for Telomere Repeat Synthesis" *Nature*, 337:331–337.
Greider (Sep. 1991) "Telomerase Is Processive" *Molecular and Cellular Biology*, 11:4572–4580.
Harley et al., (May 1990), "Telomeres Shorten During Ageing of Human Fibroblasts" *Nature*, 345:458–460.
Harley, (1991), "Telomere Loss: Mitotic Clock or Genetic Time Bomb?" *Mutation Research*, 256:271–282.
Hiyama et al., (Mar. 1995), "Correlating Telomerase activity Levels with Human Neuroblastoma Outcomes" *Nature Medicine*, 1(3):249–255.
Hiyama et al. (1992) "Length of Telomeric Repeats in Neuroblastoma: Correlation with Prognosts and Other Biological Characteristics", *Jpn. J. Cancer Res.*, 83:159–164.
Kim et al., (Dec. 1994), "Specific Association of Human Telomerase Activity with Immortal Cells and Cancer" *Science*, 266:2011–2014.
Shay et al., (1993), "Loss of Telomeric DNA During Aging May Predispose Cells to Cancer" *International Journal of Oncology*, 3:559–563.
Windle and McGuire, (Mar. 1992), "Telomeres: The Long and the Short of It" *Proceedings of the American Association for Cancer Research, Eighty–Third Annual Meeting of the American Association for Cancer Research*, 33:594–595.

Primary Examiner—W. Gary Jones
Assistant Examiner—Carla Myers
Attorney, Agent, or Firm—Melya J. Hughes; Richard L. Neeley; Kevin R. Kaster

[57] ABSTRACT

A method for predicting tumor progression and prognosing cancer comprises: (a) collecting a sample suspected of containing cancer cells; (b) analyzing the sample for telomerase activity; (c) correlating the activity with a standard level of telomerase activity; and (d) correlating a high telomerase activity with an indication of unfavorable prognosis and a low telomerase activity with a favorable prognosis.

20 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (synthetic)

(i i i) HYPOTHETICAL: NO (i v) ANTI-SENSE: NO (x i) SEQUENCE DESCRIPTION: SEQ ID NO:1:

CCCAATCCGT CGAGCAGAGT TAG　　　　　　　　　　　　　　　　　　　　23

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:2:

TAACTCTGCT CGACGGATTC CC　　　　　　　　　　　　　　　　　　　　22

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:3:

GGGTAACCCT AACCCTAACC C　　　　　　　　　　　　　　　　　　　　21

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO (x i) SEQUENCE DESCRIPTION: SEQ ID NO:4:

GGTTAGGGTT AGGGTTAAA　　　　　　　　　　　　　　　　　　　　　19

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (synthetic)

(i i i) HYPOTHETICAL: NO (i v) ANTI-SENSE: NO ( x i ) SEQUENCE DESCRIPTION: SEQ ID NO:5:

AATCCGTCGA GCAGAGTT                                                                                              18

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:6:

CCCTTACCCT TACCCTTACC CTAA                                                                                       24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:7:

TTAGGGTTAG GGTTAGGGTT AGGG                                                                                       24

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:8:

AATCCGTCGA GCAGAGTTGT GAATGAGGCC TTC                                                                             33

( 2 ) INFORMATION FOR SEQ ID NO:9:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GTGAATGAGG CCTTCGAGGC TCTGAAGAGA AGCACCCTGC TCAACCCCAA CCAGCGGCTG                                                 60

```
CCTAAGGTGG AGATCCTGCG CAGTGCCATC CAGTACATTG AGCGCCTA                    108
```

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:10:

```
CCCTTACCCT TACCCTTACC CTAATAGGCG CTCAATGTA                              39
```

( 2 ) INFORMATION FOR SEQ ID NO:11:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

```
CCCAATCCCT TACCCAATCC CTAATAGGCG CTCAATGTA                              39
```

METHODS FOR CANCER DIAGNOSIS AND PROGNOSIS

CROSS-REFERENCE TO RELATED APPLICATIONS

The present application is a continuation-in-part of U.S. patent application Ser. No. 08/315,216, filed Sep. 28, 1994, which is a continuation-in-part of Ser. No. 08/255,774, filed Jun. 7, 1994, which is a continuation-in-part of Ser. Nos. 08/151,477 and 08/153,051, both of which were filed 12 Nov. 1993, which are continuations-in-part of Ser. No. 08/060,952, filed 13 May 1993, which is a continuation-in-part of Ser. No. 08/038,766, filed 24 Mar. 1993, now issued as U.S. Pat. No. 5,489,508, which is a continuation-in-part of Ser. No. 07/882,438, filed 13 May 1992, now abandoned. Each of the foregoing patent applications is incorporated herein by reference.

ACKNOWLEDGEMENTS

This invention was supported in part by grants from the National Institute of Health (AG07992). The U.S. Government may have rights in this invention.

INTRODUCTION

1. Technical Field

The present invention relates to telomerase, a ribonucleoprotein enzyme involved in telomere DNA synthesis, and provides methods for relating the level of telomerase activity with tumor prognosis. The invention provides methods and compositions relating to the fields of molecular biology, chemistry, pharmacology, and medical diagnostic and prognostic technology.

2. Background

Telomeres are specialized structures at the ends of eukaryotic chromosomes and appear to function in chromosome stabilization, positioning, and replication (Blackburn and Szostak, 1984, *Ann. Rev. Biochem.* 53:163–194; Zakian, 1989, *Ann. Rev. Genetics* 23:579–604; Blackburn, 1991 *Nature* 350:569–573). In all vertebrates, telomeres consist of hundreds to thousands of tandem repeats of a 5'-TTAGGG-3' sequence and associated proteins (Blackburn, 1991; Moyzis et at., 1988, *Proc. Natl. Acad. Sci.* 85:6622–6626). Southern blot analysis of chromosome terminal restriction fragments (TRF) provides the composite lengths of all telomeres in a cell population (Harley et al., 1990, *Nature* 345:458–460; Allsopp et al., 1992, *Proc. Natl. Acad. Sci. USA* 89:10114–10118; Vaziri et al., 1993, *Am. J. Human Genetics*. 52:661–667). In all normal somatic cells examined to date, TRF analysis has shown that the chromosomes lose about 50–200 nucleotides of telomeric sequence per cell division, consistent with the inability of DNA polymerase to replicate linear DNA to the ends (Harley et al., 1990; Allsopp et al., 1992; Vaziri et al., 1993; Watson, 1972, *Nature New Biology* 239:197–201).

This shortening of telomeres has been proposed to be the milotic clock by which cells count their divisions (Harley, 1991, *Mut. Res.* 256:271–282), and a sufficiently short telomere(s) may be the signal for replicative senescence in normal cells (Allsopp et al., 1992; Vaziri et al., 1993; Hastie et al., 1990, *Nature* 346:866–868; Lindsey et al., 1991, *Mut. Res.* 256:45–8; Wright and Shay, 1992, *Trends Genetics* 8: 193–197). In contrast, the vast majority of immortal cells examined to date shows no net loss of telomere length or sequence with cell divisions, suggesting that maintenance of telomeres is required for cells to escape from replicative senescence and to proliferate indefinitely (Counter et al., 1992, *EMBO* 11:1921–1929; Counter et at., 1994, *Proc. Natl. Acad. Sci. USA* 91:2900–2940).

Telomerase, a unique ribonucleoprotein DNA polymerase, is the only enzyme known to synthesize telomeric DNA at chromosomal ends using as a template a sequence contained within the RNA component of the enzyme (Greider and Blackburn, 1985, *Cell* 43:405–413; Greider and Blackburn, 1989, *Nature* 337:331–337; Yu et at., 1990, *Nature* 344:126–132; Blackburn, 1992, *Ann. Rev. Biochem.* 61:113–129). With regard to human cells and tissues, telomerase activity has been identified in immortal cell lines and in ovarian carcinoma but has not been detected at biologically significant levels (that level required to maintain telomere length over many divisions) in mortal cell strains or in normal non-germline tissues (Counter et al., 1992; Counter et al., 1994; Morin, 1989, *Cell* 59:521–529). Together with TRF analysis, these results suggest telomerase activity is directly involved in telomere maintenance, linking this enzyme to cell immortality.

Scientists have therefore proposed that senescence, or mortality stage 1 (M1), occurs when there are on average several kilobases of telomeric repeats remaining and involves the anti-proliferative actions of tumor suppressor gene products such as pRb and p53 (Shay et al., 1993, *Oncogene* 8:1407). Mutations in these genes, or expression of viral transforming genes that block the action of these genes, permit cells to undergo additional divisions in the absence of telomerase until the telomeres reach a critically short length at crisis, or mortality stage 2 (M2). See Wright et al., 1989, *Mol. Cell. Biol.* 9:3088. At crisis, there is destabilization of chromosomes resulting in an increase in the frequency of dicentric chromosomes and cessation of cell proliferation. Development of an immortalized cell line after crisis is dependent on expression of telomerase activity. After crisis, telomerase can stabilize telomere length and permit indefinite cell division (Blackburn, 1994, *Cell* 77:621).

Methods for detecting telomerase activity, as well as for identifying compounds that regulate or affect telomerase activity, together with methods for therapy or diagnosis of cellular senescence and immortalization by controlling or measuring telomere length and telomerase activity, have also been described. See PCT patent publication No. 93/23572, published Nov. 25, 1993 and related U.S. patent applications Ser. Nos. 08/315,214 and 08/315,216, both filed Sep. 28, 1994, 08/255,774, filed Jun. 7, 1994, Ser. Nos. 08/151,477 and 08/153,051, both of which were filed 12 Nov. 1993, U.S. Ser. No. 08/060,952, filed 13 May 1993, and U.S. Ser. No. 08/038,766, filed 24 Mar. 1993. Each of the foregoing patent applications is incorporated herein by reference. Other methods for assaying telomerase activity in cell samples rely on the incorporation of radioactively labelled nucleotides into a telomerase substrate (Morin, 1989). The conventional assay uses an oligonucleotide substrate, a radioactive deoxyribonucleoside triphosphate (dNTP) for labelling, and gel electrophoresis for resolution and display of products. Because telomerase stalls and can release the DNA after adding the first G in the 5'-TrAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences. Although telomeric sequence oligonucleotides are efficient in vitro substrates, telomerase will also synthesize repeats using substrates comprising non-telomeric DNA sequences.

Using such methods, scientists have found that the presence of telomerase activity in somatic tissues is positively correlated with cancer (Kim et al., 1994, *Science* 266:2011–2014). U.S. application Ser. No. 08/315,216 describes the presence of telomerase activity in somatic cells as indicative of the presence of immortal cells, such as certain types of cancer cells, which can be used to make that determination even when the cells would be classified as non-cancerous by pathology.

Cancer progression is generally unpredictable, cancer diagnosis providing little guidance as to whether the cancer will progress aggressively or spontaneously regress in an individual. As an example, neuroblastoma is often described as enigmatic and unpredictable, where the incidence of spontaneous regression is much greater than in any other human cancer. Neuroblastoma arises from the embryonat neural crest and is the most common solid tumor in children younger than 5 years of age, affecting approximately 1 in 7,000 individuals (Young et al., 1986, *Cancer* 56:598–602; Sawada et al., 1991, *Am. J. Pediatr. Hematol. Oncol.* 13:3–7). Clinically, neuroblastoma tumors show remarkable biological heterogeneity, resulting in favorable prognosis in some instances and unfavorable prognosis due to aggressive growth despite multimodal therapy in other instances (Evans et at., 1976, *Natl. Cancer Inst. Monogr.* 44:49–54; Woods et al., 1992, *Pediatrics* 89:114–118; Brodeur et at., 1984 *J. Clin. Oncol.* 11:1466–1477; Brodeur et al., 1984, *Science* 224:1121–1124). About 80% of Stage IVS tumors, a particular subset of metastatic neuroblastomas defined by a localized primary tumor and distant metastasis (including liver, skin, and/or bone marrow without skeleton; Evans et al., 1976; Woods et al., 1992; Brodeur et al., 1993; Brodeur et al., 1984; D'Angio et al., 1971, *Lancet* i:1046–1049; Evans et al., 1981, *Arch. Dis. Child* 56:271–274; Kretschmar et al., 1984, *J. Clin. Oncol.* 2:799–803; Finklestein et al., 1979, *Med. Pediatr. Oncol.* 6:179–188; Evans et at., 1971, *Cancer* 27:374–378), often regress independently of anticancer therapies (Evans et al., 1981). Tumors with N-myc amplification and/or loss of heterozygosity for chromosome 1p generally have a poor prognosis (Brodeur et al., 1984; Seeger et al., 1985, *N. Engl. J. Med.* 313:1111–1116; Hayashi et al., 1989, *Cancer* 63:126–132; Fong et al., 1989 *Proc. Natl. Acad. Sci. USA* 86:3753–3757. There are two main hypotheses proposed to explain the spontaneous regression of stage IVS neuroblastoma, namely, immune surveillance resulting in immunological attack on the tumor (Hellstrom et al., 1968, *Proc. Natl. Acad. Sci. USA* 60: 1231–1238) and spontaneous maturation of the tumor (Rangecroft et al., 1978, *Arch Dis. Child* 52:815–817). Both aggressive (high S phase) and regressing (low S phase) neuroblastoma tumors contain short telomeres (Hiyama et al., 1992, *Jpn. J. Cancer Res.* 83:159–164). Because both types have shorter telomeres than normal tissues (Hiyama et at., 1992), this property cannot be used alone to differentiate between the two classes of tumors. Prognostic methods exist for other cancers, such as acute myeloid leukemia (AML), but have either given variable results or require sophisticated equipment (Vidriales et al., 1995, *British J. of Haematology,* 89: 342–348). There remains a need for simple diagnostic methods that enable a physician to differentiate aggressive tumors from less aggressive or regressing tumors, and to assess whether treatment of tumors in a patient by surgery, chemotherapy, or other means is required, and this invention meets that need.

SUMMARY OF THE INVENTION

The present invention provides diagnostic methods for differentiating low grade tumors from high grade tumors by correlating the level of telomerase activity to favorable or unfavorable prognosis. The basic method involves the following steps: (a) collecting a sample suspected of containing cancer cells; (b) analyzing the sample for telomerase activity; (c) correlating the activity with a standard level of telomerase activity; and (d) relating a high telomerase activity relative to said standard level as an indication of unfavorable cancer prognosis and a low telomerase activity relative to said standard level or a telomerase activity equal to said standard level as an indication of favorable cancer prognosis. The standard value can be a predetermined level obtained from assaying cells known to have low telomerase activity. Alternatively the standard value can be determined from a range of telomerase levels known to be associated with the different clinical outcomes of cancer progression.

The method is useful for diagnosing any cancer, and is illustrated below with reference to neuroblastoma, leukemia, and hepatocellular carcinoma. The method is used to assess the likelihood of regression or remission of neuroblastoma after treatment by, for example, surgery and chemotherapy. In a similar manner, the method can be used to assess the likelihood of remission from leukemia, in particular, acute myeloid leukemia, and to assess survival potential of a patient. Similarly, the method can be used to assess the extent of progression of hepatocellular carcinoma in an individual. Thus, the method can be performed using samples such as adrenal gland for neuroblastoma prognosis, bone marrow or blood samples for leukemia prognosis, and cells obtained from liver biopsies for hepatocellular carcinoma prognosis.

In a further aspect of the invention, the method involves assaying telomerase activity by amplification of telomerase products by a polymerase chain reaction. A control oligonucleotide is included for amplification with the telomerase products, and the relative signal obtained with the control oligonucleotide compared to that obtained with the telomerase products is used to normalize the telomerase activity level, thus allowing a more accurate estimation of telomerase activity in a sample.

In a general aspect, the present invention provides a diagnostic method that allows the physician to make a prognosis of aggressive (high grade) and less aggressive or regressing (low grade) tumors, which can then be treated accordingly, as is described in more detail below.

DETAILED DESCRIPTION AND PREFERRED EMBODIMENTS

The present invention provides methods that allow the determination of whether a tumor is aggressive or regressing and thus whether it is likely to have a clinically unfavorable or favorable prognosis. In its broadest aspect, the method of this invention entails determining the level of telomerase activity in a cell or tissue sample and correlating the level obtained with cancer and tumor progression. Thus, the method is applicable to the detection of elevated levels of telomerase activity associated with any cancer, such as neuroblastoma, gastric cancer, prostate cancer, breast cancer, colon cancer, renal cancer, ovarian/cervical cancer, liver cancer, lung cancer, and leukemia.

The methods of the present invention will typically involve the determination of the level of telomerase activity in a cell or tissue sample, which sample will often be obtained from a human, but one can also readily understand that samples tested by the present method can be obtained from agriculturally important mammals, such as cattle, horses, sheep, etc., or other animals of veterinary interest, such as cats and dogs. The assay can be carried out on any cell or tissue sample, such as blood, normal somatic tissues, germline tissues, or cancerous tissues. A "sample" is the material being analyzed which is usually subjected to pre-treatment to provide the telomerase in assayable form. This would normally entail forming a cell extract, methods for which are known in the art (for example, see Scopes, *Protein Purification: Principles and Practice*, Second Edition (Springer-Verlag, N.Y., 1987)). Preferably the detergent-based extraction protocol described below is used.

In the broader aspects of the invention, there is no limitation on the collection and handling of samples as long as consistency is maintained. Consistency of measurement of telomerase activity in clinical samples can be ensured by using a variety of techniques. For example, to control for the quality of each tissue extract, another enzymatic activity, such as alkaline phosphatase, can serve as an internal control. In addition, an internal standard can be measured concurrently with telomerase in the sample as a control for assay conditions.

The level of telomerase can be determined by detecting the telomerase ribonucleoprotein or any component thereof using methods known in the art. For example, telomerase can be detected by immunoassays using antibodies specific for telomerase. Methods for preparing antibodies and suitable immunoassays are described in *Antibodies: A Laboratory Manual*, Harlow and Lane, eds., Cold Spring Harbor, New York (1988). The antibody can be used, for example, in Western blots of two dimensional gels where the protein is identified by enzyme linked immunoassay or in dot blot (Antibody Sandwich) assays of total cellular protein, or partially purified protein. Methods for sample concentration and protein purification are described in the literature (see Scopes, 1987). For example, if desired, the telomerase present in the cell extract can be concentrated, by precipitating with ammonium sulfate or by passing the extract through a commercially available protein concentration filter, e.g., an Areicon or Millipore ultrafiltration unit. The extract can be applied to a suitable purification matrix, such as an anion or a cation exchange resin, or a gel filtration matrix, or subjected to preparative gel electrophoresis. In such cases, the telomerase and protein yield after each purification step needs to be considered in determining the level of telomerase in a sample.

Preferably, telomerase activity is measured. If desired (but not required), the telomerase can undergo further manipulations after formation of the cell extract for activity assays, as described above. However, these separations are generally difficult and may result in loss of telomerase activity, and thus, because the assay does not require purified telomerase, cell extracts that have not been pretreated are preferred for the assay.

In this invention, there are no limitations on the type of assay used to measure telomerase activity. Any of the current assays for telomerase activity can be used, as well as assays that may be developed in the future. A particularly preferred method involves the preparation of a cell extract using a detergent lysis method and the analysis of telomerase activity by the Telomeric Repeat Amplification Protocol (TRAP assay). These methods are described in detail in U.S. Ser. No. 08/315,214 entitled "Telomerase Activity Assays" and in U.S. Ser. No. 08/315,216 entitled "Telomerase Diagnostic Methods", both of which are herein incorporated by reference as noted above. The telomerase activity assays described therein involve the extension of a nucleic acid substrate by telomerase and replication of extended substrates in a primer extension reaction, such as the polymerase chain reaction (PCR).

The TRAP assay is particularly well suited for providing a variety of means to quantitate the amount of telomerase in a sample. One important means for obtaining quantitative information is the use of a control oligonucleotide template added to each reaction mixture in a known amount. An illustrative control oligonucleotide comprises, in 5'-3' order, a telomerase substrate sequence, a spacer sequence (which can be any sequence of nucleotides or length and can alter spacing of the ladder produced by electrophoresis of reaction products produced from telomerase containing samples), a telomeric repeat sequence (typically present in multiple, i.e., 2 to 50, copies), and a sequence complementary to the primer used in the assay (and so which may simply be a portion of the telomeric repeat sequence). Of course, an oligonucleotide complementary to the control sequence defined above can also serve as the control sequence, and a double-stranded control nucleic acid can also be employed.

Alternatively, one can add a control nucleic acid of any sequence to the reaction mixture in known amounts and amplify the control with primers which can be the same as or different from those used to amplify the extended telomerase substrate. The control oligonucleotide and/or the primers used to amplify the control oligonucleotide can be labelled identically to or differently from the label used to label the telomerase extension products. Use of an internal control not only facilitates the determination of whether the assay was conducted properly but also facilitates quantitation of the telomerase activity present in the sample. The detailed protocol for conducting TRAP assays using primer and internal control is described in U.S. Ser. No. 08/315,214.

Preferably, the internal standard is sufficiently large so that it will not interfere with the visualization of the telomerase ladder, such as is described in the Examples section below. Normalizing the intensity of the telomerase ladder to that of the internal standard permits the assay to become linear so that accurate comparisons between samples can be made. A weak signal resulting from the internal standard relative to that in other samples could indicate limiting PCR conditions, thus allowing the practitioner to choose to repeat the assay under non-limiting conditions, for example, by providing higher polymerase levels. The inclusion of the internal standard also immediately identifies potentially false negative tumor samples that contain, e.g., Taq polymerase (commonly used in PCR) inhibitors.

While PCR provides for exponential accumulation of primer extension products, even linear accumulation of primer extension products can provide useful results. Thus, one can use a single primer and merely make many copies of a single strand of the duplex nucleic acid that is produced when PCR is employed. Moreover, such copies can be made by means other than polymerase-mediated primer extension. Suitable methods include the ligase chain reaction (Barany, 1991, *Proc. Natl. Acad. Sci. USA* 88:189–193), nucleic acid sequence-based amplification (Compton, 1991, *Nature* 350:91–92), self-sustained sequence replication (Guatelli et al., 1990, *Proc. Natl. Acad. Sci. USA* 87:1874–1878), strand displacement amplification (Walker et al., 1992, *Proc. Natl. Acad. Sci. USA* 89:392–396), and branched DNA signal amplification (Urdea, 12 Sep. 1994, *Bio/Tech.* 12:926–928; U.S. Pat. No. 5,124,246), although the latter method involves amplification of the signal produced upon probe hybridization to a target nucleic acid. As one example, DNA ligase can be used to ligate together two oligonucleotides hybridized to a template nucleic acid. If, as in PCR, the duplex nucleic acid is then denatured, then one can repeat the process of ligation and denaturation many times to accumulate many complementary copies of the original template, i.e., the extended telomerase substrate. If one additionally adds two other oligonucleotides complementary to the copy produced by ligation of the first two oligonucleotides on the extended telomerase substrate and selects those oligonucleotides such that DNA ligase can ligate the two together to form a copy of the original extended telomerase substrate, then one has the basic components of an LCR.

To illustrate, one could employ LCR to amplify an extension product of a telomerase substrate to detect telomerase activity in a sample using the following 4 oligonucleotide "ligomers":

LTS (5'-CCCAATCCGTCGAGCAGAGTTAG-3') (SEQ ID NO:1),
CLT (5'-TAACTCTGCTCGACGGATTCCC-3') (SEQ ID NO:2),
LC (5'-GGGTAACCCTAACCCTAACCC-3') (SEQ ID NO:3), and
LG (5'-GGTTAGGGTTAGGGTTAAA-3') (SEQ ID NO:4).

The LC and CLT ligomers will anneal to an extended telomerase substrate and then be ligated with DNA ligase to form a template for ligation of the LTS and LG ligomers. These ligomers have been selected so that no two ligomers can anneal to form a duplex nucleic acid that can be joined to another duplex nucleic acid in the mixture by the blunt-end ligation activity of DNA ligase. A wide variety of such ligomers can be used in the method to minimize template-independent product formation. LCR amplification of telomerase extension products produces an amplified product of uniform size and so is conducive to quantitative analysis.

Moreover, a variety of different types of oligonucleotides can be used in telomerase activity assays. While the discussion above and Examples below illustrate assay methods with results obtained using oligodeoxyribonucleotide telomerase substrates and primers with DNA polymerase, the activity assay used in the present invention is not so limited. Thus, one can employ oligoribonucleotides or oligonucleotides that comprise one or more modified (i.e., synthetic or non-naturally occurring) nucleotides in the telomerase assay. In similar fashion, one can employ an RNA polymerase to extend a primer or to copy an extended telomerase substrate. These and other variations of the present method will be apparent to those of skill in the art upon consideration of this description of the invention.

In the diagnostic methods of the invention, the assay will be conducted to determine the level of telomerase activity present in a sample. Generally, any detectable level of telomerase activity is considered elevated in cells from normal, post-natal human somatic tissue (i.e. any level above zero) other that hematopoietic or other stem cells. The terms "low telomerase activity" and "high telomerase activity" relate to the relative levels of telomerase activities found in tumors of different clinical stages. To assess tumor prognosis, the level of telomerase in the cell extract is correlated to a standard value of telomerase activity, which is selected to divide a population of cancer patients into two statistically significant classes, those having a favorable prognosis and those having an unfavorable prognosis. In one embodiment of the invention, the standard value is selected to be the level of telomerase found in a tissue known to have low telomerase activity. For example, as is described in the Examples section below, low telomerase activity is found in fetal adrenal glands at levels similar to that in stage I, II, and IVS neuroblastoma tumors. Thus, the level of telomerase in a fetal adrenal gland sample can be chosen as the standard value representing low telomerase activity in neuroblastoma. Cultured, immortal, established cell lines are generally considered to have high levels of telomerase activity.

Alternatively, the standard level of telomerase activity is determined by collecting data to obtain a statistically significant correlation of telomerase levels with the different tumor classes. Relative levels can be determined by various methods that involve measurement of telomerase activity in aliquots of a sample under different conditions and include, but are not limited to, serial dilution of the sample, incubating sample aliquots over incrementing time periods, etc. These conditions are chosen to detect both high and low telomerase activity in at least one sample aliquot. For example, the activity assay can be carried out for a length of time sufficient to detect low telomerase activity in at least one aliquot, whereas shorter incubation times would result in detection of only high telomerase activity. Similarly, a sufficient amount of extract can be used in the activity assay to detect low telomerase activity in at least one aliquot, whereas with lesser amounts of cell or tissue extract, only high telomerase activity would be detectable. The amount of extract added can be standardized by determining the protein concentration of the extract, as is known in the art. The methods described in the Examples section below illustrate serial dilution of an extract. TRAP assays were carried out with 6, 0.6 or 0.06 µg of cell extract, where 6 µg of extract was demonstrated to be sufficient to detect both low and high telomerase activities, whereas only high telomerase activity is detected in more dilute samples. Typically, a "low telomerase activity" would be at least five, preferably at least ten, more preferably at least 50, more preferably at least 100 times less than a "high telomerase activity" under comparable conditions of measurement. One of ordinary skill in the art recognizes that if a less sensitive assay is chosen to determine the level of telomerase in a sample, it may be necessary to increase the amount of extract used or to pretreat the extract using routine methods as described above to provide detectable levels of telomerase. The assay methods do not necessarily require measurement of absolute values of telomerase, unless it is so desired, because relative values are sufficient for the methods of the present invention; however, any known method for quantitating telomerase or telomerase activity could be used for this determination.

A predetermined range of telomerase activity is established for the same cell or tissue sample obtained from subjects having known clinical outcomes by analyzing telomerase activity in aliquots of the same sample under different conditions, where such conditions allow the measurement of both high and low telomerase activities as described above. In addition, the clinical outcome of the subject from which the sample was taken is related to the measured level of telomerase activity. Sufficient measurements are made to produce a statistically significant range of values for the value to which a comparison will be made. The predetermined range of telomerase activity is typically obtained by using the same assay technique that will be used in the application of the method to an individual being tested to ensure the highest correlation. Standard values may vary with the specific cell or tissue extract for which telomerase activity is measured and with the specific assay used. The predetermined range of telomerase activity for a given cell or tissue sample can then be used to determine a standard value for the level of telomerase that would be considered low activity and correlated to favorable prognosis. The method of the invention does not require the measurement of any other substance or, in this latter described aspect of the invention, can even be dependent upon a single measurement, once a standard level for an assay procedure is established. In this case, the assay is carried out on a tumor sample under conditions that would only detect telomerase activity above the standard level or would quantitate the telomerase level.

A measured high level of telomerase activity relative to the standard value (e.g., detectable activity in more dilute samples, detectable activity in samples incubated for shorter lengths of time, etc.) is an indication of unfavorable prognosis, suggesting that the physician should employ an aggressive therapy. A measured low telomerase activity relative to the standard level or a telomerase activity equal to the standard level is an indication of favorable prognosis. The terms "favorable prognosis" and "unfavorable prognosis" are known in the art. Generally, "favorable prognosis" means that there is a likelihood of tumor regression or longer survival rates of these patients relative to those with unfavorable prognosis, whereas "unfavorable prognosis" means that the tumor is likely to be aggressive, resulting in a poor outcome for the patient. The criteria for clinical staging of cancers are also known in the art; for example, neuroblastoma staging is described by Woods et al. (1992) and Brodeur et al. (1993).

Those of skill in the art will also recognize that, while the use of cell extracts is preferred for most purposes, one can also modify the method so that intact cells can be employed. In this embodiment, one treats intact cells with the telomerase substrate oligonucleotide, following which the oligonucleotide will be extended if the cell possesses functional telomerase activity. Established in situ PCR or LCR technology with a polymerase or ligase, a primer, and nucleoside triphosphates (if a polymerase is employed) is then used on fixed cells to amplify telomerase-extended substrate oligonucleotides. Telomerase positive cells can then be detected by microscopy, utilizing, e.g., incorporation of a labelled nucleotide or oligonucleotide during primer extension. These methods are easily modified to give quantifiable data as is described above.

Although telomerase activity is present in germline cells, and low levels of telomerase activity can be detected in stem cells and certain hematopoietic system cells, such cells do not present problems for the practitioner of the present method, because germline cells can be readily distinguished and/or separated from human somatic tissue samples. Moreover, telomerase activity in hematopoietic or other stem cell samples is 1/100th or less than that of a tumor sample and thus should not interfere with analysis of samples.

The method of the present invention allows the prediction of how a cancerous condition will develop by detecting the level of telomerase activity in cancer cells, thus allowing physicians to administer an appropriate therapy. This determination of a statistically significant difference in telomerase levels in a cell or tissue extract gives a physician early warning of the tumor prognosis, even in the absence of clinical symptoms so that clinical symptoms can be closely monitored and patient treatment modified (e.g., by implementing aggressive treatment, i.e., surgery, radiation therapy, and/or chemotherapy). Assays for a given analyte, including this assay for telomerase activity, are not expected to be obtained or to be interpreted by an attending physician in the absence of additional information. Although the present method for testing the level of telomerase activity provides much useful information regarding the progression of a disease, tests that may provide additional information in conjunction with the present method include diagnostic tests for DNA ploidy, fraction of cells in S-phase, nodal status, p53, p16, p21, ms, and other oncogenes. For neuroblastoma, the age of the patient may also provide relevant information relating to the telomerase activity. As described in the Examples below, 52/60 tumors with low activity were diagnosed in patients earlier than one year of age, while 14/16 tumors in the high telomerase activity were diagnosed after one year of age ($p<0.0001$). Additionally, the results of any assay are best considered to be indicative of the probability of a presence of a clinical condition rather than as absolute proof. The same situation exists for the present invention. Nevertheless, an indication of tumor prognosis is clinically useful information and can be used by a skilled medical practitioner in combination with other information to care for patients in a more informed manner than would be possible if the information were not available. In particular, a physician can determine whether additional diagnostic tests quantitating telomerase activity should be required periodically to follow tumor progression and the effect of therapy thereon.

The methods of the invention are useful in determining the most effective tumor therapy in the case of favorable or unfavorable prognosis, and even preventing unnecessary therapy that could result in harmful side-effects when the prognosis is favorable. Thus, the present invention can be used for prognosis of any of a wide variety of cancers, including without limitation, solid tumors and leukemias including: apudoma, choristoma, branchioma, malignant carcinoid syndrome, carcinoid heart disease, carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenie, squamous cell, and transitional cell), histiocytic disorders, leukemia (e.g., B-cell, mixed-cell, null-cell, T-cell, T-cell chronic, HTLV-II-associated, lymphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's, experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia.

A preferred method of the invention allows for neuroblastoma prognosis; the prognosis for neuroblastoma prior to this invention, was particularly unpredictable. As is described in more detail in the examples below, tumor samples from 94 of 100 neuroblastoma patients were shown to have telomerase activity, whereas samples from four benign ganglioneuroma patients and 13 adjacent normal adrenal gland from neuroblastoma patients were shown to have undetectable levels of telomerase activity. Seventy-six of 79 tumor samples from untreated neuroblastoma patients with a positive telomerase signal were divided into two groups: 16 tumors (approximately 20%) had high telomerase activity (e.g., retained a TRAP signal after a 100-fold dilution of the extract); and 60 tumors (approximately 76%) had low telomerase activity. Clinically, 12 tumors (75%) with high activity and 2 tumors (3.3%) with low activity showed a poor outcome (p<0.001 ). The presence of high telomerase activity in neuroblastoma correlated with an unfavorable prognosis. Similarly, the method can be used for prognosis of hepatocellular carcinoma or leukemia, in particular AML, as is described in more detail below. The methods of the invention therefore allow the separation of cancer samples into low or high grade categories.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al., *Molecular Cloning:A Laboratory Manual*, Second Edition (1989); *DNA Cloning*, Volumes I and II (D. N. Glover, Ed. 1985); *Scopes, Protein Purification: Principles and Practice*, Second Edition (Springer-Verlag, N.Y., 1987); and *Handbook of Experimental Immunology*, Volumes I–IV (D. M. Weir and C. C. Blackwell, Eds. 1986).

The present invention also provides kits for performing the methods of the invention. Such kits can be prepared from readily available materials and reagents and can come in a variety of embodiments. For example, such kits can comprise any one or more of the following materials: reaction tubes, buffers, detergent, oligonucleotide telomerase substrates, control reagents, oligonucleotide primers, and instructions. A wide variety of kits and components can be prepared according to the present invention, depending upon the intended user of the kit and the particular needs of the user.

The following examples describe specific aspects of the invention to illustrate the invention and provide a description of the methods for those of skill in the art. The examples should not be construed as limiting the invention, as the examples merely provide specific methodology useful in understanding and practice of the invention.

EXAMPLES

EXAMPLE 1

Detection of Telomerase Activity in Neuroblastoma, Ganglioneuroma, and Putative Normal Adrenal Gland Tissue Adjacent to Neuroblastoma Extracts from neuroblastoma tumors, benign ganglioneuromas, and putative normal adrenal gland were analyzed for telomerase activity using a PCR-based assay called the "TRAP" assay (Telomeric Repeat Amplification Protocol).

Tissue Samples

Tumors were obtained from 100 neuroblastoma patients and 4 benign ganglioneuroma patients who had undergone surgery at the Hiroshima University Hospital and affiliated hospitals in Japan. Adjacent "normal" adrenal glands were obtained from 13 neuroblastoma patients. All tissues were stored at −80° C. until used.

Preparation of Cell Extracts

Cell extracts were prepared using a detergent-based extraction method. The detergent lysis method involves the lysis of the cells or tissue in a sample in a lysis buffer composed of 0.01 to 5% of a non-ionic and/or a zwitterionic detergent. A wide variety of non-ionic and/or zwitterionic detergents can be employed in the method. Preferred non-ionic detergents include Tween 20, Triton X-100, Triton X-114, Thesit, NP-40, n-octylglucoside, n-dodecylglucoside, n-dodecyl-beta-D-maltoside, octanoyl-N-methylglucamide (MECA-8), decanoyl-N-methylglucamide (MEGA-10), and isotridecyl-poly (ethyleneglycolether)$_n$, and preferred zwitterionic detergents include CHAPS (3-{(3-cholamidopropyl)-dimethylammonio}-1-propane-sulfonate), CHAPSO (3-{(3-cholamidopropyl)dimethyl-ammonio}-2-hydroxy-1-propane-sulfonate), N-dodecyl-N,N-dimethyl-3-ammonio-1-propane-sulfonate, and digitonin, with CHAPS a particularly preferred detergent. While the exact amount of detergent is not critical, 0.5 % is typically sufficient to observe enhanced extraction of telomerase activity. Diethylpyrocarbonate (DEPC)-treated, de-ionized, sterile H$_2$O was used routinely.

Frozen tissue samples of 50–100 mg were homogenized in 200 µl of CHAPS lysis buffer (0.5% CHAPS, 10 mM Tris-HCl [pH 7.5], 1 mM EGTA, 10% glycerol, 5 mM β-mercaptoethanol, 0.1 mM 4-(2-aminoethyl)benzene-sulfonyl fluoride (AEBSF; Sigma)) using Kontes tubes and dispersed with the accompanying matching disposable pestles (VWR, Sugar Land, Tex.) rotated at 450 rpm by a drill (Kim et al., 1994, *Science.* 266:2011–2015). After homogenization (avoiding excess heat), the lysates were incubated on ice for 25 minutes, and then centrifuged at 16,000 X g for 20 min. at 4° C. The supernatants were then collected and rapidly frozen and stored at −80° C. until analysis. The concentration of protein was measured using the BCA protein assay kit (Pierce Chemical Company, Rockford, Ill.).

Telomerase Assay

An aliquot of extract containing 6 µg of protein was used for each TRAP assay, a telomerase activity assay that involves the extension of a nucleic acid substrate by telomerase and replication of extended substrate in a primer extension reaction, such as the polymerase chain reaction. The reaction components include the telomerase substrate, TS (5'-AATCCGTCGAGCAGAGTT-3') (SEQ ID NO:5), which telomerase extends by synthesizing telomeric repeats and which also functions as the upstream primer in the PCR step, and the downstream primer CX, the structure of which is defined by its sequence (5'-CCCTTACCCTTACCCTTACCCTAA-3') (SEQ ID NO:6). Designed mismatches in the CX primer/extended telomerase substrate reduce interaction between the CX primer and unextended TS oligonucleotide telomerase substrate and so minimize primer-dimer (more accurately CX/TS dimer) formation.

Assay tubes were prepared by sequestering of 0.1 µg of CX primer (5'-CCCTTACCCT'FACCCTTACCCTAA-3') (SEQ ID NO:6)undera wax barrier (Ampliwax™, Perkin-Elmer, Foster City, Calif.). The assays were carried out in a total reaction volume of 50 μl. The CX primer is initially separated from the rest of the reaction mixture by a wax barrier, which melts only at the higher temperatures that mediate stringent hybridization conditions. Above the wax barrier, in addition to the extract, was a mixture providing 20 mM Tris-HCl, pH 8.3, 1.5 mM MgCl$_2$, 68 mM KCl, 0.05 % Tween 20, 1 mM EGTA, 50 μM dNTPs, $^{32}$P-dCTP, $^{32}$P-TTP, 0.1 μg of TS oligonucleotide, (5'-AATCCGTCGAGCAGAGTT-3') (SEQ ID NO:5), 0.5 μM T4 gene 32 protein (USB, Cleveland, Ohio) and 2 units of Taq DNA polymerase (Gibco BRL, Gaithersburg, Md.).

After 30 minutes incubation at room temperature for telomerase-meddiated extension of the TS primer, the reaction mixture was heated at 90° C. for 90 seconds and then subjected to 31 PCR cycles of 94° C. for 30 seconds, 50° C. for 30 seconds, and 72° C. for 45 seconds. The PCR product was electrophoresed on a 10% polyacrylamide gel and exposed to a Phosphorimager™ screen (Molecular Dynamics, Sunnyvale, Calif.). For an estimation of telomerase activity, positive extracts were reexamined by serial dilution. Extracts were diluted both 10 times and 100 times, thus, the reaction mixtures contained 0.6 μg and 0.06 μg of protein, respectively.

Telomerase activity was detected in 94 (94%) of the tumor tissues (See Table 1). In three cases in which tumor specimens were available before and after chemotherapy, telomerase activity decreased after treatment. Adjacent "normal" adrenal glands in 13 neuroblastoma patients and 4 benign ganglioneuromas were negative for telomerase activity.

TABLE 1

Telomerase activity in neuroblastoma, ganglioneuroma, and putative normal adrenal gland tissue adjacent to neuroblastoma

| Telomerase activity | undetectable | low | high |
|---|---|---|---|
| Neuroblastoma (n = 100) | 6* | 73 | 21 |
| Ganglioneuroma (n = 4) | 4 | 0 | 0 |
| Adjacent putative normal adrenal gland (n = 13) | 13 | 0 | 0 |

*of the 6 tumors without detectable telomerase activity, 3 were stage IVS, and the other 3 were tumors in which viable tumor cells were rare after multimodal chemotherapy.

Relative telomerase activities were divided into three groups: undetectable; low=positive using extracts containing 6 μg of protein but negative when diluted; high=positive using extracts containing 0.06 μg of protein (100 fold dilution). Of the neuroblastomas assayed, 66 were of adrenal origin, and 34 were of sympathetic chain origin.

Pretreatment of extracts with RNase degrades the RNA component of telomerase and abolishes activity (Greider and Blackburn, 1985, Cell 43:405–413; Greider and Blackburn, 1989, Nature 337:331–337; Morin, 1989, Cell 59:521–529). For RNase treatment, 5 μl of extract were incubated with 1 μg RNase Plus™ (5Prime→3Prime, Boulder, Colo.) for 20 min. at 37° C. Preincubation of the tissue extract with RNase to destroy the RNA component of telomerase abolished the PCR ladder.

Those of skill in the art will recognize that the reaction times, temperatures, and buffers described in this Example can vary, depending upon the needs of the practitioner, the particular substrates and primers employed, and the source of the extract and DNA polymerase.

For instance, the telomerase extension reaction can be conducted at temperatures ranging from about 10° to about 42° C. The telomerase reaction time can vary widely, depending upon the number of primer extension steps employed, the amount of telomerase expected to be in the sample, and the time available to the practitioner. Typically, the telomerase reaction time will be between 5 and 60 min., but the time could be up to several hours. In similar fashion, the PCR cycles can be composed of cycle times and temperatures that vary widely. The simplest PCR cycle comprises a duplex nucleic acid denaturation step followed by a primer annealing and extension step. While denaturation is typically carried out by heating the reaction mixture, other methods, such as helicase treatment, can be used, and the heating method itself can be conducted at a wide range of temperature for any amount of time sufficient to denature but not damage the DNA. In similar fashion, the time and temperature of the primer annealing step depends to a great extent on the reaction buffer and primer sequence, concentration, and composition, as well as the specificity required by the practitioner, while the time and temperature of the primer extension step depends greatly upon the type of DNA polymerase employed. Those of skill in the art will recognize and understand that the present invention is not limited by the times, temperatures, and variations in buffer and other reaction components that can be employed in the assay method.

EXAMPLE 2

Assay of Telomerase Activity in Untreated Neuroblastoma Cases

Because treatment of neuroblastoma results in a decrease of viable cells due to fibrosis, necrosis, and calcification, as well as potential changes in gene expression, telomerase assays were conducted on cell samples of untreated neuroblastoma obtained from human donors. The assays were conducted as described in Example 1 above. The results of the assays are shown in Table 2, below.

TABLE 2

Telomerase activity in untreated neuroblastoma cases

| Telomerase activity | undetectable (n = 3) | low (n = 60) | high (n = 16) |
|---|---|---|---|
| Age at diagnosis | | | |
| (range in months) | 6–8 | 1–96 | 7–129 |
| (median) | (8) | (7) | (20) |
| Alteration of TRFs (n = 26) | 3 | 10 | 13 |
| (reduced TRFs/elongated TRFs) | (3/0) | (10/0) | (11/2) |
| N-myc amplification | 0 | 0 | 11 |
| L-myc LOH/informative cases | 0/1 | 0/27 | 5/9 |
| Death | 0 | 2 | 12 |
| Stage | | | |
| I, II (n = 40) | 0 | 38 | 2 |
| III, IV (n = 31) | 0 | 18 | 13 |
| IVS (n = 8) | 3 | 4 | 1 |

The 76 of 79 tumors with positive telomerase signals were divided into two groups: 16 tumors (~20%) had high telomerase activity (e.g., retained a TRAP signal after a 100-fold dilution of the extract) and 60 tumors (~76 %) had low telomerase activity. Histologically, 15/16 tumors with high TRAP activity and 51/60 tumors with low TRAP activity were primarily composed of tumor cells (i.e., were stroma-poor (Shimada et al., 1984, J. Natl. Cancer Inst. 73:405–416)). There was no obvious difference in the ratio of tumor versus stromal cells of both groups of neuroblastoma, and multiple telomerase assays of the same tumor obtained from different sites gave the same results.

Variation in the intensity of TRAP signals might reflect differing amounts of the enzyme present or perhaps solubilized tissue factors that could inhibit the amplified and processive telomerase ladder. Mixing tissue extracts that were telomerase negative or expressed low activity with strongly positive extracts did not reduce the intensity of the signal. In addition, the telomerase activity was estimated by serial dilution of 6 µg of protein (standard conditions), 0.6 µg (10 fold dilution), and 0.06 µg (100 fold dilution), and no evidence of inhibition was observed. Thus, because the neuroblastoma tumors were homogeneous, and the presence of inhibitors of telomerase activity could not be detected, the relative variation in intensity of the TRAP signal is believed to reflect differing amounts of enzyme.

To control for the quality of each tissue extract, another enzymatic activity served as an internal control. Assays of alkaline phosphatase activity indicated that the extracts used to measure telomerase activity were derived from viable cells.

For statistical analysis, untreated neuroblastomas were divided into two groups: tumors with undetectable or low telomerase activity; and those with high telomerase activity (positive activity in a 100-fold diluted extract). Between these two groups, prognosis, age at diagnosis, TRF alterations and gene aberrations were compared using Fisher's exact test (Moore, D. S. and McCabe, G. P. in "Introduction to the Practice of Statistics" (1989) W. H. Freeman and Co., NY). Clinically, 12 tumors (75%) with high activity and two tumors (3.3%) with low activity showed a poor outcome ($p<0.001$). In 60 tumors with low activity, 52 were diagnosed earlier than one year of age, while 14 of 16 tumors with high activity were diagnosed after one year of age ($p<0.001$). The tumors of both types were shown to be equally homogeneous (Shimada et al., 1984). Three tumors without telomerase activity regressed.

Telomere Length Analysis and Other Biological Characteristics

Terminal restriction fragments (TRF) analysis was used as an indicator of mean telomere length and was estimated at the peak position of the hybridization signal with a $^{32}$P-labelled 5'TTAGGGTTAGGGTTAGGGTTAGGG 3' probe (SEQ ID NO:7). TRF length was analyzed in all 79 untreated tumors and compared to that of normal tissues. Peripheral blood obtained from 46 neuroblastoma patients and adjacent normal adrenal glands from 13 neuroblastoma patients were subjected to TRF analysis. The isolation of genomic DNA from tissues has been described (Hiyama et al., 1992). For TRF analysis, 2 µg of DNA were digested to completion with 10 units of Hinf I, electrophoresed on a 0.8 % agarose gel, and then blotted onto a nitrocellulose filter. The filter was hybridized to a $^{32}$P-labelled $(TTAGGG)_4$, probe, washed as previously reported (I-Iiyama et al., 1992), and then autoradiographed. The mean TRF length was estimated at the peak position of the hybridization signal. To exclude the possible effects of DNA degradation, undigested DNA was electrophoresed, and no evidence of degradation was observed. To exclude partial digestion, each filter was hybridized with a β-globin or K-ras probe (ATCC/NIH Repository Catalogue of Human and Mouse DNA Probes and Libraries (8th Edition) 1995).

Mean TRF length was reduced in 3/3 of the cases without detectable telomerase activity, while only 10/60 of the cases with low telomerase activity had reduced TRFs. However, of the cases with high telomerase activity 11/16 had reduced TRFs (<8 kb) and 2/16 had elongated TRFs (>15 kb). The lengths of TRFs of 13 adjacent normal adrenal glands, peripheral blood mononuclear cells of 46 neuroblastoma patients and 4 ganglioneuromas were analyzed and estimated to range between 8–15 kb (Hiyama et at., 1992; Hiyama et al., 1994, *Internat. J. Oncol.* 6:13–16). Ideally, the TRF length in neuroblastoma cells should be compared to that of normal adrenal glands or paravertebral ganglia in each patient. However, this normal tissue was not available from all patients examined. In the cases where normal adjacent tissues were not available, TRFs<8 kb were considered reduced and >15 kb were considered elongated. TRF lengths greater than in adjacent normal tissue is most likely due to telomerase expression in neuroblastoma increasing TRF length until TRF length reaches a stable equilibrium between telomeric loss (due to the end replication problem) and telomeric addition (due to telomerase activity). While most of the tumors (53/79) did not vary significantly in mean TRF length from adjacent putative normal adrenal tissue, 26/79 did. These 26 tumors either showed increased or decreased TRF lengths (in comparison with adjacent tissue). The alteration in TRF length (either increased or decreased) correlated significantly with high telomerase activity ($p<0.001$; Table 2). Analyses revealed reduced TRFs (<8 kb) in 24/79 of the tumor samples and elongated TRFs (>15 kb) in 2/79 tumors. Thus, 26 of the 79 tumor samples varied significantly in TRF length from adjacent normal tissue. While 13/26 (50%) of the tumors with alterations of TRF length (either increased or decreased in comparison to normal tissue) showed high telomerase activity, only 3/53 tumors (6%) without alteration in TRF lengths showed high telomerase activity (Table 2). There was a significant correlation between TRF alterations and high telomerase activity ($p<0.001$), and in 11 cases which could be followed for more than 1 year, all showed poor outcomes and/or N-myc amplification (unfavorable prognosis).

All samples were examined for amplification of the N-myc oncogene and for the loss of heterozygosity in the L-myc gene locus. N-myc amplification and loss of heterozygosity of the L-myc gene were estimated by Southern blot analysis. Genomic DNA (2 µg), prepared as described above, was digested to completion with 10 units of EcoRI, electrophoresed on a 1.0% agarose gel, and blotted onto nitrocellulose filters. The filters were separately hybridized to an N-myc probe (PN-myc-1, Oncor Inc. Gaithersburg, Md.) or to an L-myc probe (JCRB CO049) and autoradiographed (Hiyama et al., 1992). In 16 tumors with high telomerase activity, 11 had N-myc amplification. In 9 tumors with high telomerase activity, 5 had loss of heterozygosity (LOH) of the L-myc locus (1p32). These genetic changes correlated significantly with high telomerase activity ($p<0.001$) and were not detected in the tumors with low or undetectable telomerase activity.

EXAMPLE 3

Analysis of Telomerase Activity in Stage IVS in Human Neuroblastoma Tumors

Samples of human neuroblastoma tumors in stage IVS were obtained from eight patients and assays were conducted as described in Example 1 above. Telomerase activity was measured using the TRAP assay. Analysis of telomere length (TRF analysis) was performed as previously described above (Hiyama et al., 1992). N-myc amplification was estimated by Southern blot analysis. Chemotherapy was done by the regimens of the James' protocol (James et al., 1965, *JAMA* 194: 123–126), other than case #6, who was treated with an aggressive chemotherapeutic regimen for advanced stage neuroblastoma described by Sawaguchi et al., 1990, Cancer 66: 1879–1887. The results are summarized below in Table 3.

TABLE 3

Telomerase activity, TRF lengths, and N-myc amplification in Stage IVS neuroblastoma tumors.

| Case # | Age at operation | Telomerase activity | TRF tumor [Normal] kb | N-myc (copy #) | Therapy | Outcome |
|---|---|---|---|---|---|---|
| 1 | 2 mo. | low | 10.3 [12.4] | 1 | (+) | regressed |
|   | 4 mo. | low | 6.7 [11.7] | 1 |     |           |
| 2 | 3 mo. | low | 2.4 [N.D.] | 1 | (−) | regressed |
| 3 | 3 mo. | low | 8.7 [10.2] | 1 | (+) | regressed |
| 4 | 4 mo. | low | 10.7 [10.8] | 1 | (+) | regressed |
| 5 | 6 mo. | undetectable | 5.9 [N.D.] | 1 | (+) | regressed |
| 6 | 7 mo. | high | 7.0 [11.0] | 3 | (+) | deceased |
| 7 | 8 mo. | undetectable | 2.1 [11.8] | 1 | (+) | regressed |
| 8 | 8 mo. | undetectable | 5.4 [12.4] | 1 | (+) | regressed |

The putative normal lengths of TRFs were estimated by using the adjacent adrenal gland in cases #1 (at first operation) and #8 and peripheral blood mononuclear cells in case #1 (at second operation) and in cases #3, #4, #6, and #7. Normal tissue was not obtained in cases #2 and #5 [N.D. is not done].

Of the 79 untreated cases examined, eight were stage IVS, a special category of neuroblastoma that frequently regresses (Table 3). Among seven IVS neuroblastoma tumors with metastatic lesions that regressed, telomerase activity could not be detected in 3 tumors from infants 6 months or older, while low telomerase activity was present in 4 tumors from infants 4 months or younger. In one regressed tumor (case #1, Table 3), in which liver metastases were biopsied at different times, progressive TRF shortening was observed. In this case, low telomerase activity was detected but the TRF continued to shorten. One tumor (case #6, Table 3), from a stage IVS patient who did not respond to therapy, had high telomerase activity, as well as N-myc amplification, and the patient eventually died.

In the case of stage IVS neuroblastomas that regressed, TRF was always shorter than that in adjacent normal tissue, and in 7 of 8 cases, the regressed tumors had low or no telomerase activity. In one case (case #1, Table 3), the telomeres were examined two months apart, and the TRF lengths clearly shortened by several kb, suggesting that perhaps insufficient telomerase activity was present to compensate for the end-replication problem. In the regressed stage IVS tumors, low telomerase activity was detected in 4 patients younger than 4 months of age and was undetectable in 3 patients older than 6 months.

EXAMPLE 4

Analysis of Telomerase Activity in Germline Cells and Adrenal Glands in Development Human fetal adrenal gland, ovary, testis, and brain tissues were obtained from normal fetuses at 16 and 18 weeks of gestational age. Normal adrenal gland tissue was obtained from a 2-day old newborn who had a partial adrenalectomy, a 5-week old infant with congenital heart disease who had died of complications of surgery, and a 5-year old child who had died with CNS abnormalities and congenital heart disease associated with Pena-Shokier syndrome. Normal adult testis and other tissues were obtained from a 37-year old male who had died of acute heart failure. All tissues were stored at −80° C. until used. Cell extracts and telomerase activity assays were carried out as described in Example 1.

In fetal adrenal glands, neuroblasts increase in number and size until 14–20 weeks gestational age and then regress (Turkel et al., 1974, Am. J. Path. 76:225–244; Ikeda et al., 1981, J. Pediatr. Surg. 16:636–644). Thus, neuroblasts may have telomerase activity during fetal development, which activity is repressed before birth. Adrenal glands of fetuses at 16 and 18 weeks gestational age exhibited telomerase activity, while no activity was detected in normal adrenal glands in a newborn, a 2-month-old infant, or a 5-year-old boy. Other tissues examined revealed telomerase activity in fetal ovary, fetal testis, and adult testis but not in fetal or juvenile brain (0/4). Ser. dilutions of each fetal tissue extract indicated that inhibitors were unlikely to be the explanation for the variation in levels of activity. Thus, in some respects, low telomerase activity in the fetal adrenal glands is similar to that in stage IVS tumors that are likely to regress (characteristic of younger infants and repressed in older infants) and Stage I and II neuroblastomas. Most of these tumors were detected in infants less than one year old who did not exhibit other gene aberrations (such as N-myc amplification). Although not all stage I, II, and IVS tumors regress, especially in stage IVS neuroblastoma tumors, the combination of insufficient telomerase activity and telomere shortening may eventually result in spontaneous tumor cell death, perhaps by apoptosis (Prichard et al., 1994, Lancet 344: 869–870). The levels of telomerase activity in unfavorable neuroblastomas (stage III and IV) were higher than those of fetal adrenal glands. The tumors with poor prognosis had several genetic changes (e.g. N-myc amplification, L-myc LOH), in addition to high telomerase activity, and none regressed.

EXAMPLE 5

Assay of Telomerase Activity in Acute MVeloid Leukemia (AML)

AML is a highly aggressive disease resulting from aberrant proliferation and maturation of progenitor stem cells. AML samples were obtained from 41 patients at MD Anderson, Houston, Tex. Extracts from the AML samples were prepared and analyzed for telomerase activity as described in Examples 1 and 2, above. The results of the assay are shown in Table 4, below.

TABLE 4

| Number of Patients | Telomerase Activity at Diagnosis | Weeks after Diagnosis until Death* |
|---|---|---|
| 10 | +++ | 21 weeks |
| 5 | ++ | 41 weeks |
| 20 | +/− | 87 weeks |

*indicates pooled data
+++ indicates measurable activity with 0.06 μg of extract.
++ indicates measurable activity at 0.6 μg extract.
+/− indicates measurable activity only with 6 μg of extract or no measurable activity in an extract.

Six patients who are still alive (125–254 weeks after diagnosis) had either undetectable or low telomerase activity at diagnosis. Patients with undetectable or low activity generally had a higher survival rate than did those with higher activity levels. The results show that over a 4-fold higher survival rate is seen with patients having undetectable or low telomerase activity relative to patients having very high activity (+++) at diagnosis.

EXAMPLE 6

Telomerase Activity in Hepatocellular Carcinoma Tissues and in Hepatic Tissues from Noncancer Patients Hepatocellular carcinoma tissues and hepatic tissue samples were obtained from 33 patients at MD Anderson, Houston, Tex. Extracts from the samples were prepared and analyzed for telomerase activity as described in Examples 1 and 2, above. The results of the assay are shown in Table 5 below.

During the advancing stages of hepatocellular carcinoma, the tumor cells become less differentiated and generally increase in size. All samples of the most advanced stage of hepatocellular carcinoma had strong telomerase activity, whereas lower levels of telomerase activity were found only in samples from earlier stages of hepatocellular carcinoma. Normal liver samples did not have any detectable telomerase. In addition to carcinoma tissues, diseased liver samples were tested for telomerase activity. In some cases, both trace and weak telomerase activity levels were found in liver samples from patients having acute hepatitis, chronic hepatitis, or liver cirrhosis. Because these conditions are known to increase the risk of liver cancer, these measured telomerase levels may indicate the presence of tumor cells in amounts too low to be detected by standard methods and thus a likelihood of developing liver cancer.

TABLE 5

| Tissues | Telomerase Activity$^a$ (# Telomerase positive/tested) | | | | | |
|---|---|---|---|---|---|---|
| | A | B | C | D | — | (total) |
| Hepatocellular Carcinoma (HCC) Stages | | | | | | |
| well differentiated | 4 | 0 | 1 | 0 | 2 | 5/7 |
| moderately differentiated | 14 | 4 | 0 | 1 | 3 | 19/22 |
| poorly differentiated | 4 | 0 | 0 | 0 | 0 | 4/4 |
| Total | 22 | 4 | 1 | 1 | 5 | 28/33 |
| Size (diameter) | | | | | | |
| smaller than 2 cm$^b$ | 4 | 1 | 1 | 0 | 2 | 6/8 |
| between 2 and 3 cm$^c$ | 9 | 0 | 0 | 0 | 1 | 9/10 |
| larger than 3 cm | 9 | 3 | 0 | 1 | 2 | 13/15 |
| Total | 22 | 4 | 1 | 1 | 5 | 28/33 |
| Normal | 0 | 0 | 0 | 0 | 4 | 0/4 |
| Chronic Liver Diseases | | | | | | |
| Acute Hepatitis | 0 | 0 | 1 | 4 | 2 | 5/7 |
| Chronic Hepatitis | 0 | 0 | 3 | 11 | 17 | 14/31 |
| Liver Cirrhosis | 0 | 0 | 1 | 5 | 2 | 6/8 |
| total | 0 | 0 | 5 | 20 | 21 | 25/46 |

$^a$Relative telomerase activity levels are as follows: (A) strong, detectable in 100× (or more) diluted sample; (B) moderate, detectable in 10× diluted sample; (C) weak, detectable in 1× diluted sample; (D) trace, detectable in 1× diluted sample only after longer exposure periods than standard procedure; and (−) negative, not detectable in 1× diluted sample even after long exposure.
$^b$All but one which was moderately differentiated were well differentiated.
$^c$All were moderately differentiated.

EXAMPLE 7

Quantitative TRAP Assay

This example demonstrates the quantitation of the TRAP assay using an internal 150 bp standard that permits the telomerase ladders to be normalized for the decreased efficiency f amplification as products accumulate. The sequences described below were chosen solely to illustrate quantitation of the TRAP assay. Other primers and/or internal sequences could be used equally effectively to produce the internal standard for quantitation.

The 150 bp standard was prepared as follows. Modified TS and CX oligonucleotides were synthesized so that each contained an extra 15 nucleotides at the 3' end that overlapped with the myogenin cDNA encoding amino acids 97 to 132 of the helix-loop-helix region. The sequences were as follows:

Modified TS primer:
5' AATCCGTCGAGCAGAGTTGTGAATGAGGCCTTC 3' (SEQ ID NO: 8)

Myogenin Sequence:
5' GTGAATGAGGCCTTCGAGGCTCTGAA-GAGAAGCACCCTGCTCAACCCCAACC AGCG-GCTGCCTAAGGTGGAGATCCTGCGCAGT-GCCATCCAGTACATTGAGCGCC TA 3' (SEQ ID NO:9)

Modified CX primer:
5' CCCTTACCCTTACCCTTACCCTAATAG-GCGCTCAATGTA 3' (SEQ ID NO: 10)

Alternatively, the modified CX primer can have the following sequence:

Modified CX primer:
5' CCCAATCCCTTACCCAATCCCTAATAG-GCGCTCAATGTA 3' (SEQ ID NO: 11)

The positions of the priming sites were designed so that the final PCR product would be 150 bp long, near but slightly higher that the TRAP ladders in all but the most intense ladders. Once amplified using these modified oligonucleotides, the 150 nucleotide product can be reamplified using the standard TS and CX oligonucleotides.

Human 293 kidney cell extracts were prepared for the quantitative TRAP assays essentially as decribed in Example 1. TRAP assays were carried out using the reaction conditions described in Example 1 with the above 150 bp nucleotide product added as the internal standard and employing the standard CX and TS oligonucleotides as primers for amplification of the telomerase ladders and internal standard. Various combinations of parameters were studied (see Table 6) and then scanned using a Phosphorimager apparatus. Peaks were manually defined so that a first peak was the internal standard and a second peak included all of the telomerase ladder peaks (therefore it is the sum of all the radioactive peaks, not any individual peak). The results showed that a $10^9$ dilution of a 35 ng/μl stock solution of the 150 bp standard in the TRAP buffer could be easily detected using the TRAP assay and showed a decreased amplification under conditions where Taq polymerase was limiting.

TABLE 6

|  | Sample 1 | Sample 2 | Sample 3 | Sample 4 |
|---|---|---|---|---|
| Taq Polymerase | 2 U | 7 U | 7 U | 7 U |
| Dilution of Internal Standard | $10^9$ | $10^9$ | $10^9$ | $10^9$ |
| Number of Cells | 100 | 10 | 100 | 1000 |
| Signal from 150 bp Standard (Phosphorimager units) | 46.6 K | 130 K | 124 K | 53 K |
| Signal from Telomerase Products (Phosphorimager units) | 23.7 K | 9.9 K | 49 K | 261 K |
| Telomerase Products/150 bp Standard | 0.51 | 0.075 | 0.40 | 5.02 |

The signal with 100 cells as input for 31 cycles with either 2 U (Sample 1) or 7 U (Sample 3) of Taq polymerase was compared. The raw signal from the telomerase ladder was about twice as great with 7 U of Taq. However, when the raw signal was normalized to the internal standard (i.e., by determining the ratio of the two values), virtually identical values (0.4 versus 0.5, thus within 20% of each other) were obtained. Similarly, when 10, 100 and 1000 cells were assayed (Samples 2, 3 and 4, respectively), there was less than a two-fold variation from linearity over the entire 100-fold dilution (the normalized 10-cell signal was 67-fold less than the 1000 cell signal). These dilutions were made by adding 1 μl (35 ng) of standard to each reaction. Linearity could be improved by making a large stock of TRAP buffer containing a uniform concentration of the standard. The extremely low concentration of the TS oligo (and the fact that the internal standard is double stranded), results in the internal standard not being elongated by telomerase under TRAP conditions and thus it migrates as a distinct single band even if included in the assay from the very beginning (as opposed to addition after the 90° C. step of the TRAP assay).

Taq polymerase inhibitors have been observed in samples in which a signal is not obtained initially but in which a telomerase ladder appears once the sample is diluted. The inclusion of the 150 bp internal standard not only allows the TRAP assay to be quantitative, but also automatically identifies such samples, because the inhibition of Taq polymerase (or any other polymerase the practitioner may choose to use) will prevent amplification of the internal standard. The incidence of undetected false negatives is thus substantially reduced.

To test whether whole cells rather than just cell extracts could be analyzed, aliquots of a dilute cell suspension containing single cells or three cells were identified under direct microscopic examination. These aliquots were then diluted with TRAP assay buffer in which the concentration of Tween-20 detergent had been increased to 0.5% to ensure cell permeablization and then transferred to TRAP assay tubes. The TRAP assay was carried out as described above, other than that the incubation time was increased from 30 min to one hour, and the number of PCR cycles was increased from 31 to 34. Telomerase ladders were observed from aliquots having three cells and from single cells, thus demonstrating the sensitivity of the assay.

As described above, one of ordinary skill in the art recognizes that the method described above could be easily modified to use different primer sequences (e.g., the TC and ACT sequences described above), different internal sequences other than that encoding myogenein which can be cDNA, genomic DNA fragments, or synthetic nucleic acids, etc. The internal standard is not limited by size other than the extent of its amplification should be equivalent or easily correlated to that of the telomerase ladder and its signal is easily separated from that of the telomerase ladder. Similarly, amplification of the telomerase products and internal standard or their signal is not limited to the use of PCR, as is described in detail above.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for prognosing cancer in humans, said method comprising:
    (a) collecting a sample suspected of containing tumor cells;
    (b) analyzing said sample for telomerase activity;
    (c) correlating said activity with a standard level of telomerase activity; and
    (d) correlating a high telomerase activity with an indication of unfavorable prognosis and a low telomerase activity with a favorable prognosis.

2. The method of claim 1, wherein said analyzing in step (b) comprises preparing a cell extract.

3. The method of claim 2, wherein said analyzing in step (b) is under conditions selected to detect any telomerase activity, and said method further comprises analyzing a second aliquot of said sample for telomerase activity under conditions selected to detect telomerase activity only above said standard level of activity; and associating high telomerase activity to the presence of telomerase in both said first and second aliquots and low telomerase activity to the presence of telomerase only in said first aliquot.

4. The method of claim 3, wherein said second aliquot is diluted at least 10-fold relative to the first aliquot.

5. The method of claim 3, wherein said second aliquot is at least 100-fold diluted relative to the first aliquot.

6. The method of claim 1, wherein said analyzing step comprises incubating said aliquot in a reaction mixture comprising a telomerase substrate and a buffer in which telomerase can catalyze the extension of said telomerase substrate, and determining whether said telomerase substrate has been extended by addition of telomeric repeat sequences.

7. The method of claim 6, wherein said analyzing step further comprises amplifying any extended telomerase substrates in said reaction mixture by a polymerase chain reaction using at least one primer complementary to a telomeric repeat sequence.

8. The method of claim 6, wherein said analyzing step further comprises amplifying a control oligonucleotide in said reaction mixture by a polymerase chain reaction.

9. The method of claim 8, wherein said method further comprises normalizing a first signal obtained with said extended telomerase substrates with a second signal obtained with said control oligonucleotide.

10. The method of claim 1, wherein said tumor cells are neuroblastoma cells.

11. The method of claim 10, wherein said standard level is the level of telomerase activity in a fetal adrenal gland cell extract.

12. The method of claim 1, wherein said sample is an adrenal gland sample.

13. The method of claim 1, wherein said sample is removed from tissue adjacent to a neuroblastoma tumor.

14. The method of claim 1, wherein said sample is of sympathetic chain origin.

15. The method of claim 1, wherein said tumor cells are hepatocellular carcinoma cells.

16. The method of claim 1, wherein said sample is a liver sample.

17. The method of claim 1, wherein said tumor cells are leukemic cells.

18. The method of claim 17, wherein said leukemic cells are from a patient with acute myeloid leukemia.

19. The method of claim 1, wherein said favorable prognosis is tumor regression.

20. The method of claim 1, wherein said favorable prognosis is indicative of longer survival rates relative to patients with unfavorable prognosis.

* * * * *